United States Patent [19]
Dahms et al.

[11] Patent Number: 5,911,981
[45] Date of Patent: Jun. 15, 1999

[54] SURFACTANT BLENDS FOR GENERATING A STABLE WET FOAM

[75] Inventors: Gerd H. Dahms, Velbert, Germany; James W. Cook, Crystal Lake, Ill.

[73] Assignee: R.I.T.A. Corporation, Woodstock, Ill.

[21] Appl. No.: 08/957,128

[22] Filed: Oct. 24, 1997

[51] Int. Cl.[6] .............................. A61K 7/075; A61K 7/17; B01F 17/56; C11D 1/72
[52] U.S. Cl. ........................... 424/70.19; 424/70.21; 424/70.22; 424/73; 510/123; 510/135; 514/944; 514/945; 514/975; 516/14; 516/15; 516/19
[58] Field of Search .................... 252/307, 356; 510/123, 135; 424/70.19, 70.21, 70.22, 73

[56] References Cited

U.S. PATENT DOCUMENTS

| | | | |
|---|---|---|---|
| 2,733,252 | 1/1956 | Thompson et al. | 260/410.9 |
| 2,744,825 | 5/1956 | Thompson et al. | 99/91 |
| 2,789,992 | 4/1957 | Thompson et al. | 260/410.9 |
| 3,033,686 | 5/1962 | Landfried et al. | 99/91 |
| 3,141,030 | 7/1964 | Buddemeyer et al. | 260/410.9 |
| 3,275,503 | 9/1966 | Marnett et al. | 514/547 |
| 3,472,940 | 10/1969 | Osipow et al. | 514/785 |
| 3,636,017 | 1/1972 | Eng | 260/410.9 |
| 3,728,447 | 4/1973 | Osipow et al. | 424/70.22 |
| 4,184,978 | 1/1980 | France et al. | 252/309 |
| 4,198,311 | 4/1980 | France et al. | 252/117 |
| 4,301,820 | 11/1981 | Cannell et al. | 132/7 |
| 4,424,820 | 1/1984 | Cannell et al. | 132/7 |
| 4,663,069 | 5/1987 | Llenado | 252/307 X |
| 4,758,376 | 7/1988 | Hirota et al. | 424/70.19 X |
| 4,761,279 | 8/1988 | Khalil et al. | 424/73 |
| 4,822,601 | 4/1989 | Goode et al. | 424/59 |
| 5,002,680 | 3/1991 | Schmidt et al. | 252/90 |
| 5,011,681 | 4/1991 | Ciotti et al. | 424/81 |
| 5,429,815 | 7/1995 | Faryniarz et al. | 424/47 |
| 5,490,955 | 2/1996 | Hagan et al. | 510/127 |
| 5,496,538 | 3/1996 | Zimmerman et al. | 424/45 |
| 5,534,500 | 7/1996 | Casamassina et al. | 252/356 X |
| 5,744,062 | 4/1998 | Dahms et al. | 252/312 |

OTHER PUBLICATIONS

Osipow et al., "Fatty Acid Lactylates," Reprint No. R.13, in *Drug and Cosmetic Industry,* Mar., Apr., May 1969.

Jennings et al., "Use of acyl lactylates in cosmetics and toiletries," *Chemical Abstracts,* 84:21965t (1976).

*Primary Examiner*—Richard D. Lovering
*Attorney, Agent, or Firm*—Marshall, O'Toole, Gerstein, Murray & Borun

[57] ABSTRACT

Surfactant blends that generate a stable spherical foam are disclosed. The surfactant blends contain a nonionic surfactant or an amphoteric surfactant as the principal foaming agent, and a sufficient amount of an acylate lactylate to enhance foam volume and provide a foam that remains in a spherical form for up to about forty minutes. A method of generating a long-lasting foam also is disclosed.

16 Claims, 7 Drawing Sheets

SURFACTANT BLENDS FOR GENERATING A STABLE WET FOAM

FIELD OF THE INVENTION

The present invention relates to surfactant blends capable of generating a large volume of a stable foam. More particularly, the present invention relates to surfactant blends containing: (a) a nonionic surfactant, an amphoteric surfactant, or a mixture thereof, as the primary foaming agent, and (b) an acyl lactylate in a sufficient amount to enhance foam volume and provide a foam that remains in a wet, or spherical, form for up to about forty minutes. The present invention also relates to a method of improving the foam volume and foam stability of aqueous compositions by incorporating a surfactant blend into the aqueous composition.

BACKGROUND OF THE INVENTION

Foam is an important property of cleaning compositions, and especially personal care compositions, such as hair shampoos, body gels, dentifrices, and shaving creams. Esthetically, foam is an important property because consumers equate a rich, long-lasting foam to a high quality product that works well. Functionally, foam is an important property because the foam first acts as a carrier to deliver cleaning surfactants to the skin or hair, then acts as a carrier to help remove emulsified soil and sebum from the cleaned skin or hair.

However, to achieve these esthetic and functional goals, the foam must be present in a wet, or spherical, form. If the generated foam is unstable, the foam changes from the wet form to the dry, or hexagonal, form relatively quickly, i.e., in less than about two minutes. Dry foam bubbles break quickly, and, therefore, for dermatogically preferred compositions do not provide the esthetic and functional foam properties typically required for consumer acceptance of the composition.

Foam is created by dispersing air or a gas in a surfactant-containing liquid. The mechanism of dispersing a gas in a surfactant-containing liquid is similar to the dispersion of two immiscible liquids during formation of an emulsion. Consequently, gas bubbles dispersed in a liquid are stabilized in the same manner as emulsions, i.e., by formation of surfactant layers at the gas-liquid interface. The surfactant layers keep the gas bubbles separated and prevent "coalescence," i.e., the merging of small gas bubbles to form larger gas bubbles. In general, more dense and more compact surfactant layers form smaller bubbles and retard the coalescence mechanism.

Figure 1:
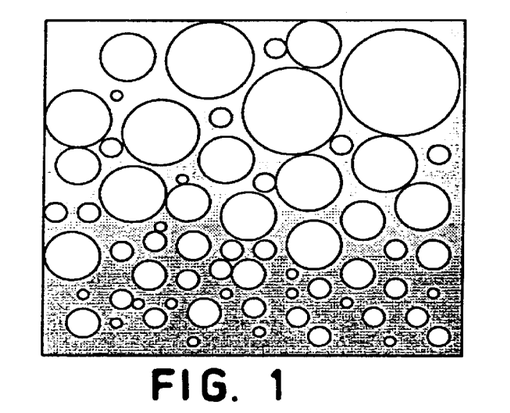
FIG. 1 schematically illustrates a wet foam having spherical bubbles.

It is well known that because of the very large density difference between the dispersed gas and the liquid, the gas bubbles rise to the top of the liquid. The enriched concentration of gas bubbles at the top of the liquid appear as "foam." Initially, all of the gas bubbles in the foam are spherical, as illustrated in FIG. 1. FIG. 1 shows that there is sufficient space between each individual spherical gas bubble for the presence of the surfactant-containing liquid, and the foam behaves like an emulsion. This is termed a "wet foam."

Figure 2:
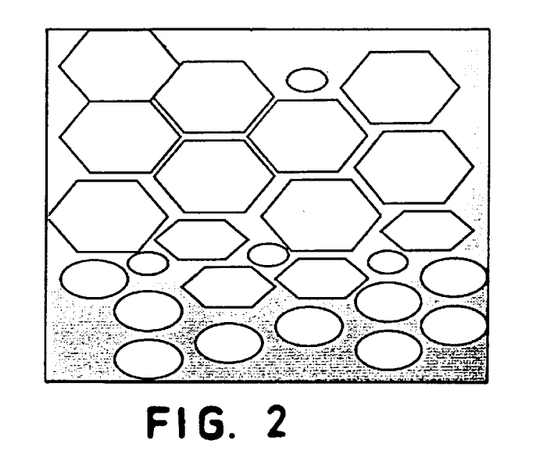
FIG. 2 schematically illustrates the transformation of a wet foam to a dry foam having hexagonal bubbles.

Over time, the liquid present in the interstices between the individual gas bubbles drains out due to gravity. Depending on the nature and chemical structure of the surfactant in the liquid, lamellar liquid crystalline layers form and arrange at the gas-liquid interface. If the lamellar layers have a low viscosity, the surfactant-containing liquid between individual gas bubbles drains relatively easily, and the spherical form of the foam bubbles changes into a hexagonal form relatively quickly. Hexagonal bubbles quickly break. The transition of a foam from the spherical form to the hexagonal form due to foam aging is illustrated in FIG. 2. Foam in the hexagonal form is termed a "dry foam." Dry foams are unstable, which leads to a rapid reduction in foam volume due to rapidly breaking bubbles.

However, if the lamellar surfactant layers have a high viscosity, the transition from a spherical foam to the hexagonal form is delayed. The speed of the transition of a foam from the spherical to hexagonal form determines how the foam is used in practical applications, and also determines how the foam is perceived esthetically. For example, for shampoos and shower gels, foams having a foam transition of about two minutes or less, i.e., a metastable foam structure, is required. A more stable foam could lead to insufficient wetting and distribution of the surfactant on the skin or hair, because during application of the shampoo or shower gel to the skin or hair, the surfactant drains from between the bubbles to contact the hair or skin. Then, by continual rubbing of the shampoo or shower gel on the skin or hair, new foam bubbles are generated, which act as a carrier to remove soil and sebum from the skin or hair.

Other foam applications, e.g., shaving foams, require a foam having a much greater stability because the applied foam is not regenerated by continual rubbing techniques and because of the relatively long time required to complete the entire shaving operation. Furthermore, a controlled and sufficient wetting of the hair and skin is required for a smooth shaving operation. Sufficient wetting occurs only if the surfactant-containing liquid can drain from the foam lamellae to contact the skin, and drainage can occur only if the foam bubbles are in the spherical form.

Figure 3:
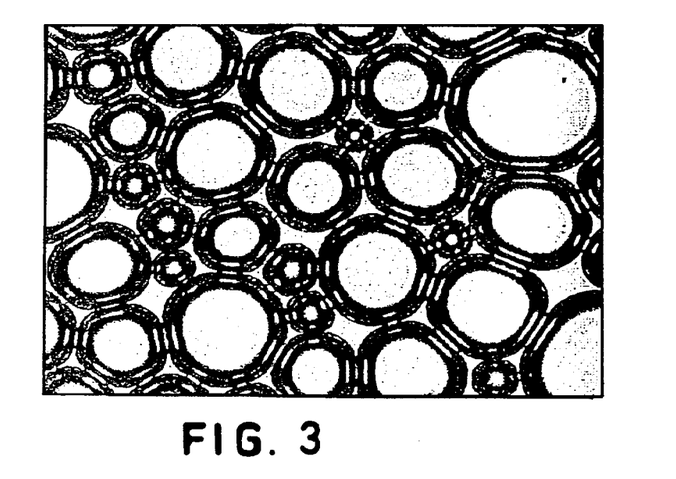
FIG. 3 illustrates spherical bubbles, the stabilizing lamellar liquid crystalline layers of surfactant surrounding each bubble, and the presence of a liquid in the interstices between bubbles.
Figure 4:
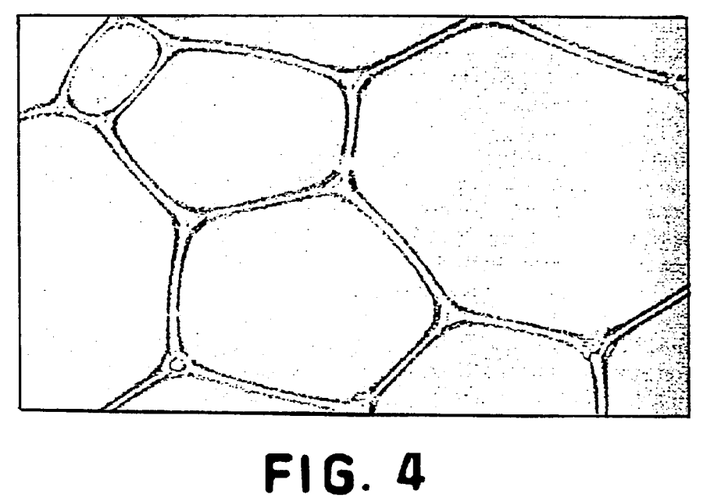
FIG. 4 illustrates a dry foam.

The difference in structure between a wet, spherical foam and a dry, hexagonal foam is illustrated in FIGS. 3 and 4. FIG. 3 clearly shows both the lamellar liquid crystalline surfactant structure that stabilizes each bubble of a wet foam and the large amount of surfactant-containing liquid between individual bubbles. The relatively thick surfactant structure illustrated in FIG. 3 also retards the coalescence of neighboring bubbles into a single, larger bubble. In contrast, FIG. 4 shows a lack of a stabilizing surfactant structure around the hexagonal bubbles and the relative absence of surfactant-containing liquid between the bubbles.

The most commonly used sulfated anionic surfactants are well known for providing a high volume of a stable foam, and having an excellent ability to emulsifying soils and oils, i.e., to act as an efficient cleaner of skin and hair. Sulfated anionic surfactants include the anionic sulfates and the anionic sulfonates. Accordingly, sulfated anionic surfactants have been the primary surfactant used in shampoos and other skin and hair cleaning products. However, sulfated anionic surfactants have disadvantages. For example, the sulfated anionic surfactants strip the hair of natural oils that condition the hair, and thereby can damage the hair and give freshly shampooed hair a dry, "creaky" feel. Sulfated anionic surfactants also are harsh to the skin and eyes, therefore making sulfated anionic surfactants unsuitable for use in baby shampoos or pet products.

Amphoteric and nonionic surfactants are mild to the skin and eyes, and do not strip the hair of natural oils. However, amphoteric and nonionic surfactants generate a poor foam in comparison to a sulfated anionic surfactant. Therefore, shampoos and similar cleaners based primarily on amphoteric and nonionic surfactants have not met good consumer acceptance. But, amphoteric and nonionic surfactants have been used in conjunction with sulfated anionic surfactants in attempts to provide a shampoo that takes advantage of the foaming properties of a sulfated anionic surfactant, while tempering the disadvantageous properties of the sulfated anionic surfactant with a nonionic or amphoteric surfactant.

It would be desirable, therefore, to provide a composition that is based primarily on a nonionic or amphoteric surfactant, and that can be free of a sulfated anionic surfactant, yet provides a copious foam volume that remains in the wet, or spherical, form for up to forty minutes. The present invention is directed to such compositions, and to a method of enhancing the foam volume and stability of an amphoteric or nonionic surfactant.

SUMMARY OF THE INVENTION

The present invention is directed to surfactant blends capable of generating a large volume of a stable, wet foam. The surfactant blend contains a nonionic surfactant, an amphoteric surfactant, or a mixture thereof, as the primary foaming agent. The surfactant blend also contains an acyl lactylate in a sufficient amount to enhance foam volume, and to provide a foam that remains in a wet, or spherical, form for up to about forty minutes. A wet foam of desired stability for a particular practical application can be achieved by selecting a proper combination of primary foaming agent and acyl lactylate.

In accordance with an important aspect of the present invention, the surfactant blends contain about 0.1% to about 25%, by weight of the blend, of an acyl lactylate, and about 75% to about 99.9%, by weight of the blend, of a primary foaming agent. The primary foaming is selected from the group consisting of a nonionic surfactant, an amphoteric surfactant, and mixtures thereof. Preferred primary foaming agents comprise a betaine, an alkamidopropyl betaine, a sulfobetaine, an alkyl polyglycoside, an alkylamphocarboxylate, or a mixture thereof.

Another important aspect of the present invention is to provide a surfactant blend containing a sufficient amount of an acyl lactylate having the general structural formula:

wherein RCO is a $C_6$ to $C_{14}$ acyl radical; a is a number from 1 to 3, and typically 1 to 2; M is an alkali metal, an alkaline earth metal, ammonium, or a substituted ammonium group having one or more $C_1$ to $C_3$ alkyl or hydroxyalkyl groups. The preferred RCO acyl radicals are $C_8$ to $C_{12}$ acyl radicals.

Another aspect of the present invention is to improve the foam volume and foam stability of aqueous compositions by incorporating a surfactant blend of the present invention into the composition.

The above and other advantages and novel features of the present invention will become apparent from the following detailed description of the preferred embodiments of the invention.

DETAILED DESCRIPTION OF THE PREFERRED EMBODIMENTS

Numerous personal care compositions rely upon the formation of a rich, stable foam for efficacy and consumer acceptance. These personal care compositions include, for example, shaving creams, dental products, shampoos, shower gels, and hair mousses. Desirable foam properties have been achieved using a sulfated anionic surfactant. However, sulfated anionic surfactants have disadvantages, and investigators have attempted to substitute nonionic and amphoteric surfactants for sulfated anionic surfactants to overcome these disadvantages. To date, such attempts have been relatively unsuccessful because of the poor foaming properties exhibited by nonionic and amphoteric surfactants. The present invention, therefore, is directed to surfactant blends that overcome the poor foaming properties of nonionic and amphoteric surfactants, and permits their increased use in personal care compositions.

The present invention is directed to surfactant blends comprising: (a) a primary foaming agent selected from the group consisting of an amphoteric surfactant, a nonionic surfactant, and a mixture thereof, and (b) an acyl lactylate. The acyl lactylate is present in a sufficient amount to enhance foam volume and provide a foam that remains in a wet, or spherical, form for up to about forty minutes. Preferably, the surfactant blend is free of a sulfated anionic surfactant. As used herein, the term "free of a sulfated anionic surfactant" is defined as meaning that a sulfated anionic surfactant is not intentionally added to a surfactant blend of the present invention, but may be present as a by-product or contaminant in the primary foaming agent or the acyl lactylate, i.e., a surfactant blend contains 0% to about 0.1% by weight of a sulfated anionic surfactant.

The surfactant blends provide a copious, stable foam, and demonstrate the additional features of viscosity enhancement, clarity, mildness to the skin and eyes, and biodegradability of compositions containing the surfactant blends. The surfactant blends demonstrate an enhanced ability to generate a stable foam, wherein the foam generated by a particular surfactant blend is more stable than a foam generated solely by the nonionic and/or amphoteric surfactant present in the surfactant blend.

The primary foaming agent of the surfactant blend is selected from the group consisting of a nonionic surfactant, an amphoteric surfactant, and a mixture thereof. The primary foaming agent is present in the surfactant blend in an amount of about 75% to about 99.9%, and preferably in an amount of about 80% to about 99%, by weight of the surfactant blend. To achieve the full advantage of the present invention, the primary foaming agent is present in an amount of about 85% to about 98%, by weight of the surfactant blend.

The identity of the nonionic surfactant and/or amphoteric surfactant present in the primary foaming agent is not limited, as long as the nonionic or amphoteric surfactant has an ability to generate a foam in aqueous solution. Accordingly, a nonionic surfactant used in the primary foaming agent has an HLB value of at least about 6, i.e., an HLB value of about 6 to about 25. Preferred, nonionic surfactants have an HLB value of about 8 to about 20, and, to achieve the full advantage of the present invention, about 12 to about 18.

The HLB value of a nonionic surfactant is a well-known term to persons skilled in the art. Furthermore, the HLB value of a particular nonionic surfactant either is published or can be estimated from published formulations. For example, the HLB value of a particular nonionic surfactant can be estimated by dividing the weight percent of the hydrophilic portion of the surfactant by five, e.g., for nonionic ethoxylates, the weight percent of oxyethylene in the surfactant. The HLB values for commercially available nonionic surfactants typically are published in well-known reference sources, such as *McCutcheon's Detergents and Emulsifiers, North American Edition*, 1993 Annual, pages 229–246, published by McCutcheon Division, MC Publishing Co., Glen Rock, N.J., incorporated herein by reference.

Although the identity of the nonionic surfactant is not otherwise limited, preferred nonionic surfactants contain a hydrophobic moiety, such as an aromatic or aliphatic moiety having a carbon chain of about 8 to about 30 carbon atoms, and particularly about 12 to about 20 carbon atoms; and further include a sufficient number of hydrophilic moieties, such as alkylene oxide moieties, like ethoxy or propoxy moieties. The hydrophobic carbon chain is etherified with a sufficient amount of ethylene oxide and/or propylene oxide to provide a water-soluble nonionic surfactant.

Nonionic surfactants are well-known materials and have been used in personal care compositions. Suitable nonionic surfactants for use in the present surfactant blends include, but are not limited to, compounds in the classes known as block copolymers of ethylene oxide and propylene oxide, ethoxylated alcohols, ethoxylated alkylphenols, alkyl polyglycosides, and mixtures thereof.

In particular, the nonionic surfactant can be an ethoxylated alkylphenol, i.e., a condensation product of an alkylphenol having an alkyl group containing about 6 to about 12 carbon atoms in either a straight chain or branched chain configuration with ethylene oxide, the ethylene oxide being present in an amount equal to at least about 8 moles ethylene oxide per mole of alkylphenol. Examples of compounds of this type include nonylphenol condensed with about 9.5 moles of ethylene oxide per mole of phenol; dodecylphenol condensed with about 12 moles of ethylene oxide per mole of phenol; dinonylphenol condensed with about 15 moles of ethylene oxide per mole of phenol; octylphenol condensed with about ten moles of ethylene oxide per mole of phenol; and diisooctyl phenol condensed with about 15 moles of ethylene oxide per mole of phenol. These ethoxylated alkylphenol nonionic surfactants are designated in the *CTFA INTERNATIONAL COSMETIC INGREDIENT DICTIONARY, FOURTH ED.*, The Cosmetic Toiletry and Fragrance Association, Washington, D.C. (1991) (hereinafter the *CTFA Dictionary*) as octoxynols, nonoxynols, dodoxynols and nonyl nonoxynols.

The ethoxylated alcohols, i.e., condensation products of aliphatic alcohols having about 8 to about 22 carbon atoms with about 8 to about 25 moles of ethylene oxide, also are useful nonionic surfactants. The alkyl chain of the aliphatic alcohol can be either straight or branched, primary or secondary. Preferred nonionic surfactants are the condensation products of alcohols having an alkyl chain containing about 10 to about 20 carbon atoms with from about 8 to about 15 moles of ethylene oxide per mole of alcohol. Examples of such ethoxylated alcohols include the condensation product of myristyl alcohol with about 10 moles of ethylene oxide per mole of alcohol; and the condensation product of coconut alcohol (a mixture of fatty alcohols with alkyl chains varying in length from about 10 to about 14 carbon atoms) with about 12 moles of ethylene oxide. Numerous ethoxylated alcohols (and ethoxylated alkylphenols) are listed in the *CTFA COSMETIC INGREDIENT HANDBOOK, FIRST EDITION*, The Cosmetic, Toiletry and Fragrance Association (1988) (hereinafter the *CTFA Handbook*), pages 4–6, incorporated herein by reference.

Especially preferred nonionic surfactants are the alkyl polyglycosides. Alkyl polyglycosides are disclosed in numerous patents, such as for example Llenado U.S. Pat. No. 4,565,647. The alkyl polyglycosides have a hydrophobic group containing about 6 to about 30 carbon atoms, preferably about 10 to about 16 carbon atoms, and a polysaccharide, e.g., a polyglycoside, hydrophilic group containing about 1.5 to about 10, preferably about 1.5 to about 3, and most preferably about 1.6 to about 2.7, saccharide units. Any reducing saccharide containing 5 or 6 carbon atoms can be used, e.g., glycose, galactose and galactosyl moieties can be substituted for the glucosyl moieties.

Optionally, a polyalkylene oxide chain can join the hydrophobic moiety and the polysaccharide moiety. The preferred alkylene oxide is ethylene oxide. Typical hydrophobic groups include alkyl groups, either saturated or unsaturated, branched or unbranched containing about 8 to about 18, preferably about 10 to about 16, carbon atoms. Preferably, the alkyl group is a saturated, straight chain alkyl group. The alkyl group can contain up to about 3 hydroxy groups, and the polyalkylene oxide chain can contain up to about 10, preferably less than 5, alkylene oxide moieties. Suitable alkyl polysaccharides are octyl, nonyl, decyl, undecyl, dodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, galactoses, and mixtures thereof. Suitable mixtures include coconut alkyl di-, tri-, tetra-, and pentaglucosides and tallow alkyl tetra-, penta-, and hexaglucosides.

The preferred alkyl polyglycosides have the formula

RO $(C_nH_{2n}O)_t(\text{glycosyl})_x$, wherein R is selected from the group consisting of alkyl, alkylphenyl, hydroxyalkyl, hydroxyalkylphenyl, and mixtures thereof wherein the alkyl group contains about 10 to about 18, preferably about 12 to about 14, carbon atoms; n is 2 or 3; t is a number from 0 to about 10, preferably 0; and x is a number from about 1.3 to about 10, preferably from about 1.3 to about 3, most preferably from about 1.3 to about 2.7. The glycosyl preferably is derived from glucose. Especially useful nonionic surfactants are the alkyl polyglycosides like decyl polyglucose and lauryl polyglucose, available commercially as PLANTAREN™ 2000 and PLANTAREN™ 1300 from Henkel Corporation, Emery Group Cospha, Ambler, Pa.

The laurate esters of sorbitol condensed with at least about 20 moles of ethylene oxide also are useful nonionic surfactants. Exemplary nonionic surfactants in this class include polysorbate 20, polysorbate 21, polysorbate 40, polysorbate 60, polysorbate 61, polysorbate 65, polysorbate 80, polysorbate 81, and polysorbate 85, as designated in the *CTFA Dictionary*.

The nonionic surfactant included in the surfactant blend of the present invention also can be an ether of a polyol and a sugar, a polyethylene glycol, or a condensation product of ethylene oxide with a long chain amide. These nonionic surfactants, as well as numerous others not cited herein, are well known to persons skilled in the art and are fully described in the literature, such as *McCutcheon's Detergents and Emulsifiers, North American Edition,* 1993 Annual, published by McCutcheon Division, MC Publishing Co., Glen Rock, N.J.

As will be demonstrated in detail hereinafter, a nonionic surfactant having an HLB of at least about 6, and the ability to form an aqueous composition that generates an initial foam height of at least about 120 ml (milliliters), is useful in the present invention. Therefore, in addition to the above-listed classes of nonionic surfactants and the above-listed specific nonionic surfactants, numerous other nonionic surfactants having an HLB of at least about 6 and the ability to generate an initial foam height of at least 120 ml, i.e., 120 ml or greater, also are useful in the present surfactant blend.

The foam height of an aqueous solution of the nonionic surfactant is determined by adding 0.2 grams (g) of the composition to 100 ml tap water in a stoppered 500 ml graduated cylinder. The graduated cylinder then is completely inverted 10 times. The foam height is measured within 5 seconds for initial foam height, and is measured again after 5 minutes. The reported foam heights include the 100 ml of water.

Further examples of specific, useful nonionic surfactants include, but are not limited to, C11-15 pareth-12, C11-15 pareth-20, C12-15 pareth-9, C12-15 pareth-12 C22-24 pareth-33, ceteareth-10 through ceteareth-55, ceteth-10 through ceteth-45, dodoxynol-12, isoceteth-10, isolaureth-10, isosteareth-12, isosteareth-20, laneth-20, laureth-10 through laureth-40, decyl polyglucose, lauryl polyglucose, acid, nonoxynol-10 through nonoxynol-50, nonyl nonoxynol-10, octoxynol-10 through octoxynol-70, oleth-10 through oleth-50, PEG-10 oleate through PEG-36 oleate, trideceth-15, laneth-15, beheneth-20, isoceteth-20, isosteareth-10, octyldodeceth-20, steareth-16, and mixtures thereof. Numerous other nonionic surfactants are listed in the *CTFA Cosmetic Ingredient Handbook, First Ed.,* The Cosmetic Toiletry and Fragrance Assn., Inc., Washington, D.C. (1988) at pages 87 through 97, incorporated herein by reference.

Amphoteric surfactants have the ability to foam, and, accordingly, selection of an amphoteric surfactant as the primary foaming agent is not limited. Preferred classes of amphoteric surfactants include the betaines, alkamidopropyl betaines, sulfobetaines (i.e., sultaines), alkylamphocarboxylates, phosphobetaines, phosphitaines, n-alkylamino propionates, n-alkylamino dipropionates, and imidazolines. Numerous classes of amphoteric surfactant, and individual amphoteric surfactants, are disclosed in U.S. Pat. No. 3,929,678, incorporated herein by reference.

Examples of betaines include, but are not limited to, the alkylbetaines and alkamidopropyl betaines, such as cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgamma-carboxypropylbetaine, lauryl-bis(2-hydroxypropyl)carboxyethylbetaine, cocamidopropyl betaine, lauramidopropyl betaine, coco-oleamidopropyl betaine, and the like. Examples of sultaines include, but are not limited to, cocodimethylpropylsultaine, stearyldimethylpropylsultaine, laurylbis(2-hydroxyethyl) propylsultaine, cocamidopropyl hydroxysultaine, tallowamidopropyl hydroxysultaine, dihydroxyethyl tallow glycinate, and the like. Examples of aminosultaines include, but are not limited to, cocamidodimethylpropylsultaine, stearylamidodimethylpropylsultaine, laurylamido-bis(2-hydroxyethyl)propylsultaine, and the like.

Phosphobetaines include, but are not limited to, lauric myristic amido 3-hydroxypropyl phosphobetaine, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, and the like. Phosphitaines include, but are not limited to, cocamido propyl monosodium phosphitaine, lauric myristic amido propyl monosodium phosphitaine, and the like.

The n-alkylamino propionates and n-alkylimino dipropionates include, but are not limited to, compounds having the structures:

wherein R' is an alkyl or hydroxyalkyl group having 8 to 22 carbon atoms and X is hydrogen, ammonium, or an alkali metal.

In addition to the primary foaming agent, the surfactant blend also contains an acyl lactylate to enhance foam properties and to provide a stable wet foam. The acyl lactylate is present in the surfactant blend in an amount of about 0.1% to about 25%, and preferably about 1% to about 20%, by weight of surfactant blend. To achieve the full advantage of the present invention, the acyl lactylate is present in an amount of about 2% to about 15%, by weight of the surfactant blend.

The amount and identity of acyl lactylate present in the surfactant blend is determined by the identity of the primary foaming agent, by the desired foam volume, and by the type of composition into which the surfactant blend is incorporated. For example, if the composition is a shaving cream, a sufficient amount of acyl lactylate is incorporated into the surfactant blend to provide a wet foam that is stable for several minutes. If the composition is a body gel, the amount of acyl lactylate can be decreased because a wet foam is needed for less than two minutes.

Likewise, the amount of acyl lactylate in the surfactant blend can be varied depending on the inherent foaming ability of the primary foaming agent and the desired foam volume. These parameters are well known to formulators working in the art, such that the amount of acyl lactylate required in the surfactant blend to provide an enhanced foam volume of increased stability can be readily determined.

Acyl lactylates used in the surfactant blend have the general structural formula:

wherein RCO radical is a $C_6$ to $C_{14}$ acyl radical; a is a number from 1 to 3, and typically 1 to 2; M is an alkali metal, an alkaline earth metal, ammonium, or a substituted ammonium group having one or more $C_1$ to $C_3$ alkyl or hydroxyalkyl groups. The preferred RCO acyl radicals are $C_8$ to $C_{12}$ acyl radicals, and the preferred M is ammonium or an alkali metal.

The acyl lactylates and their method of manufacture are described in various patents, for example, U.S. Pat. Nos. 2,733,252; 2,744,825; 2,789,992; 3,033,686; and 3,141,030. Various acyl lactylates also are available commercially. Commercial acyl lactylates typically are a blend of the monolactylate (i.e., a=1) and the dilactylate (i.e., a=2), and contain small amounts of trilactylate (i.e., a=3). As used herein, the term "acyl lactylate" is defined as either a pure monolactylate, a pure dilactylate, a pure trilactylate, or a commercial mixture containing the mono-, di-, and trilactylates.

Examples of acyl lactylates having the above general structure include, but are not limited to, sodium lauroyl monolactylate, sodium myristoyl monolactylate, sodium decanoyl monolactylate, potassium dodecanoyl monolactylate, potassium dodecanoyl dilactylate, sodium myristoyl dilactylate, sodium lauroyl dilactylate, triethanolammonium (TEA) dodecanoyl monolactylate, ammonium decanoyl monolactylate, triethanolammonium decanoyl monolactylate, sodium caprooyl lactylate, sodium capryloyl lactylate, sodium caproyl lactylate, sodium cocoyl lactylate, sodium lauroyl lactylate, monoethanolammonium (MEA) lauroyl lactylate, and potassium lauroyl lactylate.

For illustrative purposes, the following idealized structures depict sodium caproyl lactylate and sodium lauroyl lactylate, respectively:

The acyl lactylate is used in conjunction with the primary foaming agent to provide a surfactant blend which, after incorporation into an aqueous composition, provides a copious amount of stable foam. The foam remains in the wet, or spherical, form for up to forty minutes. The foam generated by the surfactant blend is more stable than a foam generated solely by the primary foaming agent, wherein the foam remains in the wet form two to ten times longer than a foam generated solely by the primary foaming agent. The amount of the increase in foam stability is related to the identity of the primary foaming agent and acyl lactylate, and the amount of acyl lactylate present in the surfactant blend.

A formulator can readily determine the proper amount of acyl lactylate to use in conjunction with the primary foaming agent in order to provide a surfactant blend capable of yielding the foam properties required for a particular type of aqueous composition. The foam properties required of the aqueous composition are related to the end use of the composition, and are well known to persons skilled in the art.

The ability of the surfactant blends of the present invention to provide an enhanced foam properties and enhanced wet foam stability have been tested. In these tests, the present surfactant blends were compared to high foaming sulfated anionic surfactants. As previously stated, the present surfactant blends preferably are free of sulfated anionic surfactants. As described hereafter, the present surfactant blends demonstrate improved foaming properties attributable to the presence of acyl lactylates.

An acyl lactylate improves the performance of nonionic and amphoteric surfactants in a similar way that an alkanolamide improves the properties of anionic surfactants. However, the present surfactant blends, which contain an amphoteric and/or nonionic surfactant and an acyl lactylate, are improved over the anionic surfactant-alkanolamide blends because the present surfactant blends are much milder to the skin and eyes, and are more readily biodegraded.

As discussed above, aqueous cleaning compositions produce a foam during application on skin or hair. The freshly produced foam is distributed over the skin or hair during the application process, and acts as a carrier for the surfactants in the composition. During the cleaning process, a portion of the foam lamellae break down and deliver the surfactant to the skin or hair. The surfactant then wets the skin or hair, and emulsifies the grease and soil. During continued rubbing, the soiled surfactant solution is "refoamed" into foam lamellae. This "soiled" foam then is rinsed from the skin or hair.

The form of the foam structure is important to the cleaning process because an incorrect foam structure reduces, or even stops, the distribution of the surfactant between the skin or hair and the foam. During the skin or hair wetting process, it is important that the surfactants in the cleaning composition are delivered by foam lamellae having a low viscosity. For efficient cleaning, it is important that the foam has a sufficient stability and compatibility with soil, such that the soil is emulsified and then transported in the foam for removal from the skin or hair.

One of the best known cleaning surfactants in the personal care industry is sodium lauryl sulfate (SLS), and, consequently, SLS was used as a standard for evaluating the foaming properties of the present surfactant blends. The foaming properties of SLS are demonstrated in a foam generated by an 8 wt. % aqueous solution of SLS.

Figure 5:
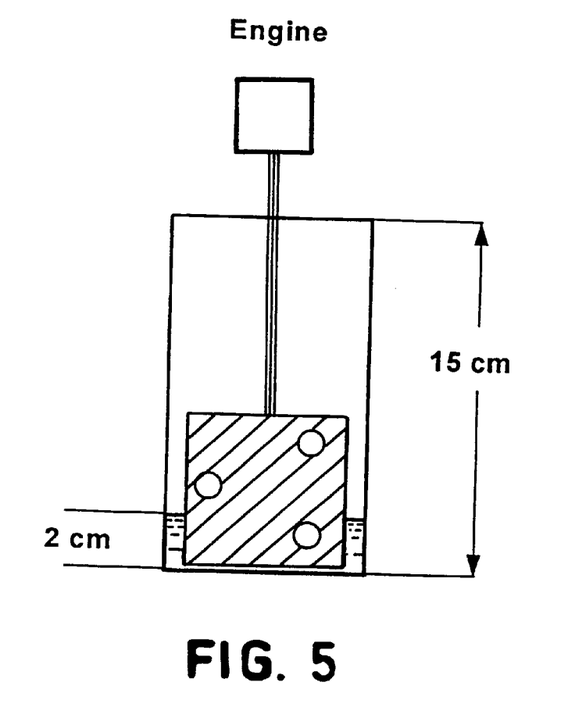
FIGS. 5 and 6 illustrate an apparatus and method used to generate a foam.
Figure 6:
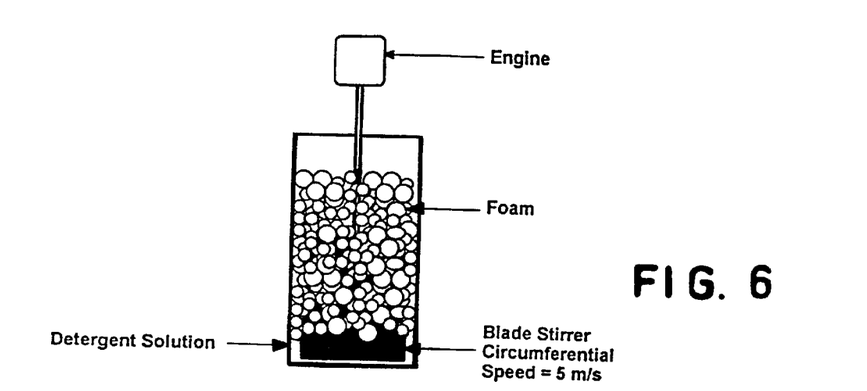

The foam was generated using 100 ml (milliliters) of an aqueous solution containing 8 wt. % of SLS. The solution was placed in a 600 ml beaker, then the surfactant solution was stirred with a blade stirrer, as illustrated in FIGS. 5 and 6, at a circumferential speed of 5 m/s (meters/second) for 10 min (minutes). Then, the foam was analyzed. All foams tested herein were generated by this method. The foams were evaluated by observation under a microscope (i.e., an Olympus BH2 microscope) using polarized light at 100× magnification. The foams were evaluated essentially immediately after formation, and again after 15 minutes of aging.

Figure 7:
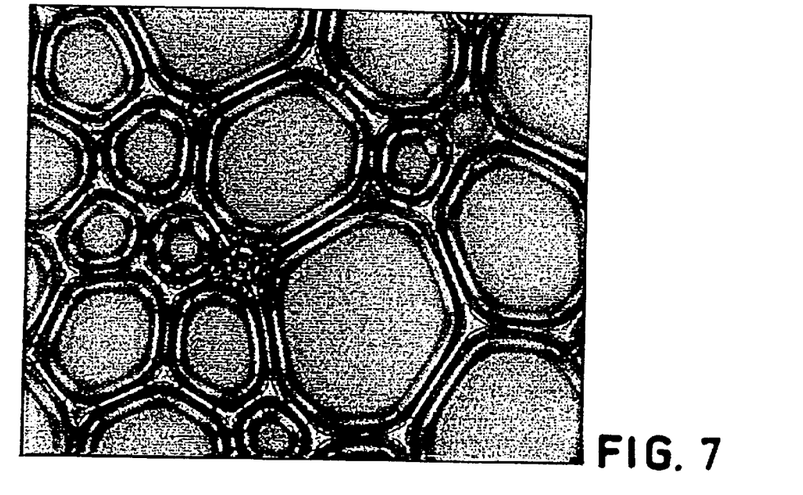
FIGS. 7 and 8 illustrate the foam structure of an 8 wt. % aqueous solution of sodium lauryl sulfate (SLS) immediately after foam generation and after aging for 15 minutes, respectively.
Figure 8:
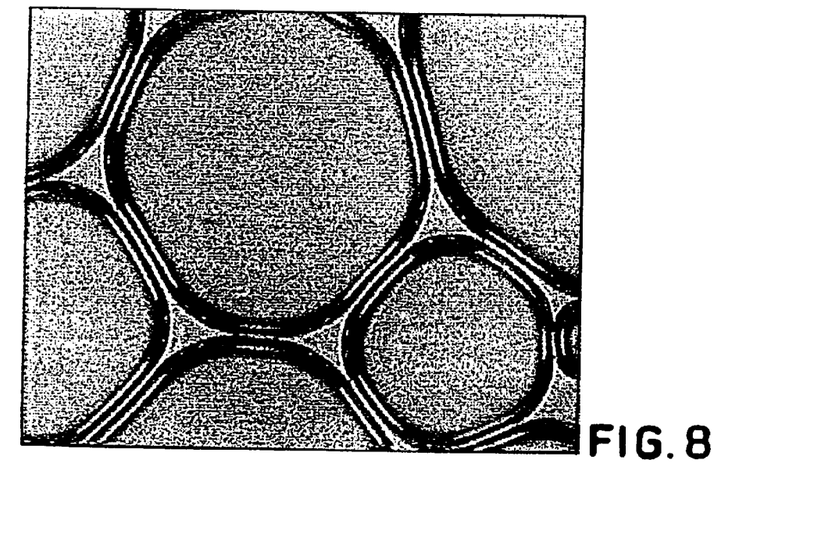

FIGS. 7 and 8 illustrate the foam structure generated by an 8 wt. % aqueous solution of SLS. As illustrated in FIG. 7, SLS initially produced a foam having a semipolyhedral structure having distinct lamellar liquid crystalline structures. After aging for 15 min, the semipolyhedral form of the bubbles was maintained, but the thickness of the lamellae was reduced, thereby indicating draining of the aqueous phase from the foam, as illustrated in FIG. 8. The foam structure depicted in FIGS. 7 and 8 illustrates a standard requirement for a good foam.

Figure 9:
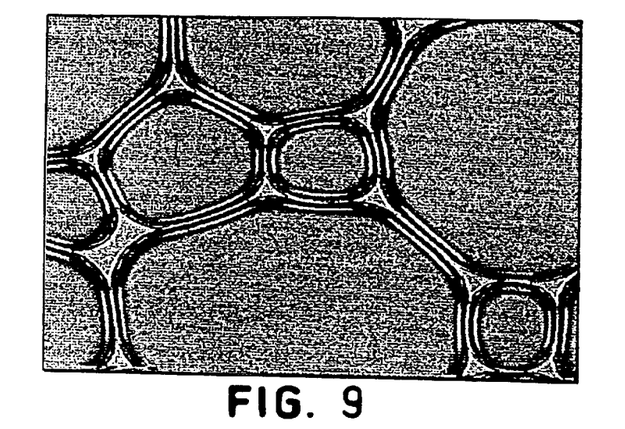
FIGS. 9 and 10 illustrate the foam structure of an 8 wt. % aqueous solution of cocamidopropyl betaine immediately after foam generation and after aging for 15 minutes, respectively.
Figure 10:
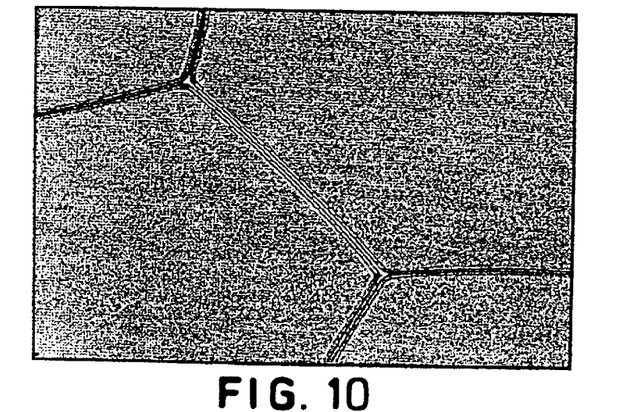

The SLS foam shown in FIGS. 7 and 8 was compared to a foam generated by an aqueous solution of cocamidopropyl betaine. Cocamidopropyl betaine is known to produce a foam that is inferior to SLS. The initial foam structure generated by cocamidopropyl betaine is illustrated in FIG. 9, which shows a foam of similar structure to a foam generated by SLS, but with less distinct surfactant lamellae and bigger sized bubbles than in FIG. 7. FIG. 10 shows that, after 15 min of aging, the surfactant lamellae have drained completely, indicating that the foam has only a limited stability during application and usage.

Figure 11:
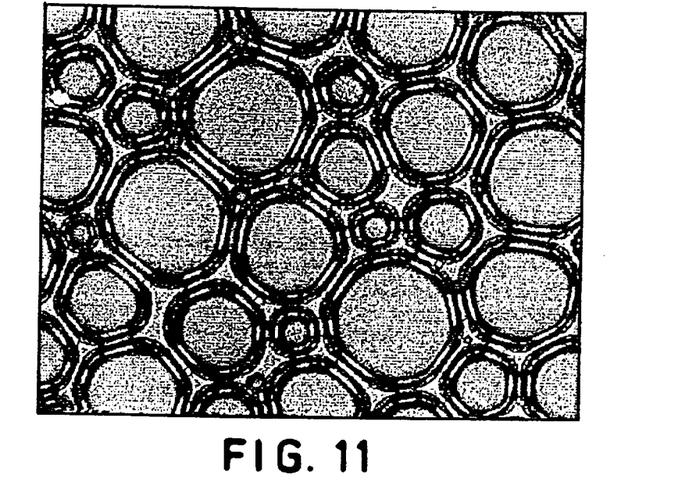
FIGS. 11 and 12 illustrate the foam structure of an aqueous solution containing 0.8 wt. % sodium caproyl lactylate and 7.2 wt. % cocamidopropyl betaine immediately after foam generation and after 15 minutes of aging, respectively.
Figure 12:
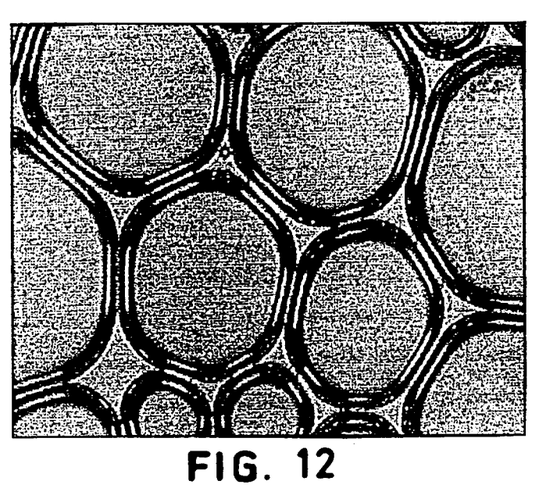
Figure 13:
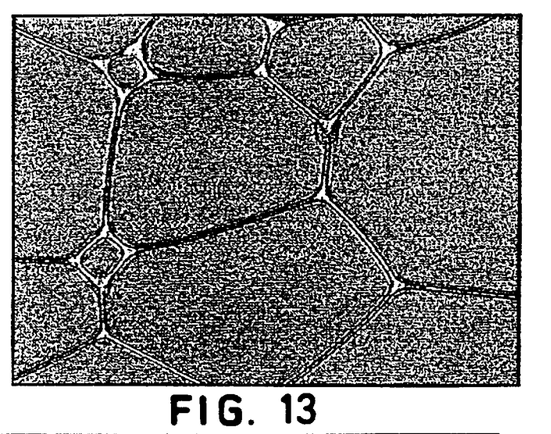
FIGS. 13–16 illustrate the foam structure of an aqueous solution containing 6.5 wt. % cocamidopropyl betaine and 1.6 wt. % of sodium capryloyl lactylate, sodium caproyl lactylate, MEA lauroyl lactylate, or TEA lauroyl lactylate, respectively, after 15 minutes of aging.
Figure 14:
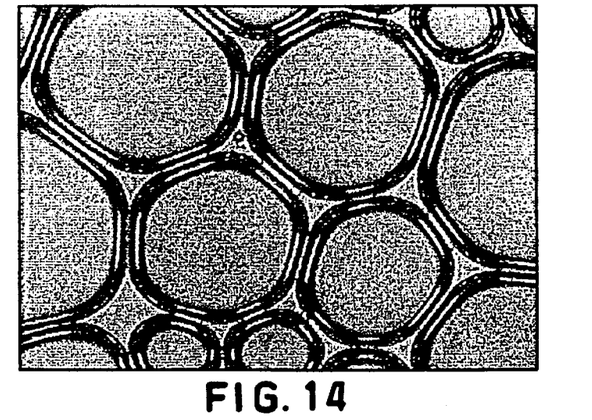
Figure 15:
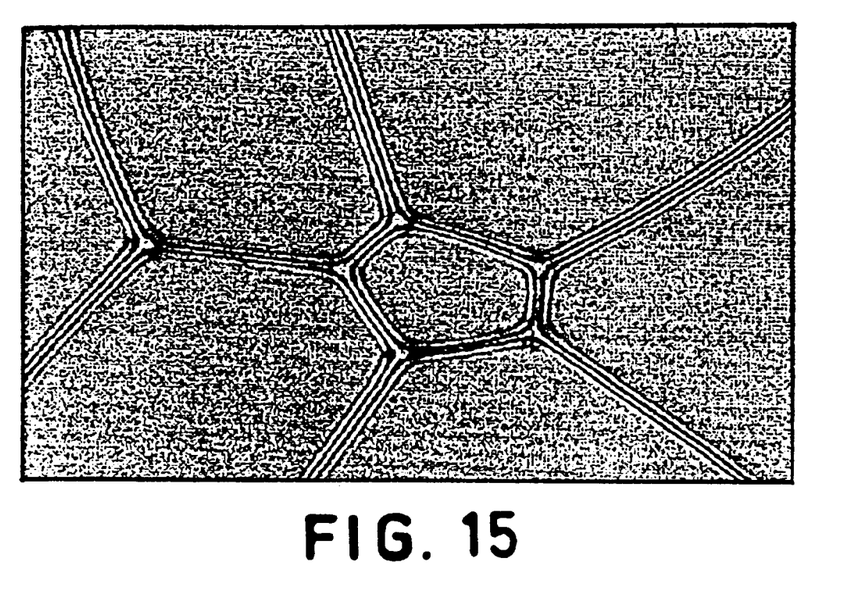
Figure 16:
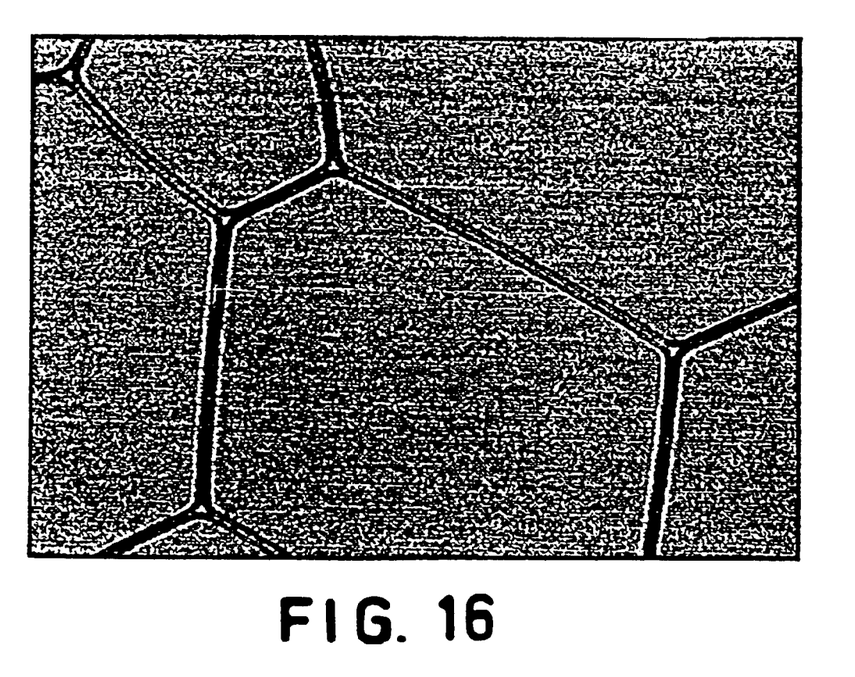

To demonstrate the ability of an acyl lactylate to improve the foam structure of an amphoteric or nonionic surfactant, a betaine was used as the primary foaming agent and was blended with sodium caproyl lactylate, sodium capryloyl lactylate, sodium caproyl lactylate, or sodium lauroyl lactylate, in a weight ratio of cocamidopropyl betaine to acyl lactylate of 90/10, 80/20, and 70/30. In every test, the foam structure of the betaine was improved by the addition of an acyl lactylate. Surprisingly, incorporating sodium caproyl lactylate, at weight ratio 90/10 (i.e., 0.8 wt. % sodium caproyl lactylate and 7.2 wt. % betaine in demineralized water), produced a foam that was essentially identical to the foam structure of the pure SLS solution, both immediately after foam generation and after aging the foam for 15 min, as illustrated in FIG. 11 and FIG. 12, respectively.

To more fully investigate the foam structures, freshly prepared foams were evaluated rheologically. The Theological test was based on a flow analysis using a parallel plate rheometer, wherein one of the plates was based on an acrylic and the gap between the plates was 2000 μm. The results of this Theological test are set forth in Tables 1 and 2, which summarize the viscosity, in mPa*s, of freshly prepared foams. Table 1 summarizes the viscosity of an SLS foam and a cocamidopropyl betaine foam, wherein no acyl lactylate is present. Table 2 summarizes the viscosities of cocamidopropyl betaine solutions containing a varying amount of six different acyl lactylates. The theological test showed that adding a relatively small amount of an acyl lactylate to a betaine modifies the foam of the betaine to achieve a foam structure similar, or identical, to a foam structure provided by SLS. In particular, an aqueous solution containing 0.8 wt. % of sodium caproyl lactylate and 7.2% cocamidopropyl betaine provided a foam essentially identical to an 8 wt. % aqueous solution of SLS, as demonstrated above in Tables 1 and 2 and in a comparison between FIGS. 7 and 8 and FIGS. 11 and 12.

TABLE 1

Viscosity (mPa*s) of Foam of 8 wt. % Aqueous Solutions

| | |
|---|---|
| Sodium lauryl sulfate | 70 |
| Cocamidopropyl betaine | 50 |

TABLE 2

Viscosity (mPa*s) of Foam vs. Acyl Lactylate Concentration

| | Concentration of Acyl Lactylate in a Betaine Solution[1] | | |
|---|---|---|---|
| | 0.8 wt. % | 1.6 wt. % | 2.4 wt. % |
| Sodium caprooyl lactylate | 50 | 50 | 50 |
| Sodium capryloyl lactylate | 55 | 166 | 609 |
| Sodium caproyl lactylate | 70 | 1,331 | 1,600 |
| Sodium lauroyl lactylate | 62 | 457 | 2,433 |
| MEA lauroyl lactylate[2] | | 122 | |
| TEA lauroyl lactylate[3] | | 56 | |

[1] Total surfactant concentration is 8.0 wt. %;
[2] MEA is monoethanolammonium;
[3] TEA is triethanolammonium.

In another test, the foaming viscosity of pure acyl lactylates were determined, and are summairized in Table 3. The data summarized in Table 3, coupled with the data summarized in Table 2, show that a preferred acyl lactylate for use in the present surfactant blends contain a $C_8$–$C_{12}$ acyl radical because such acyl lactylates provide a more viscous foam.

TABLE 3

Viscosity (mPa*S) of 8 wt. % Solutions of Acyl Actylates

| | |
|---|---|
| Sodium capryloyl lactylate | 2,740 |
| Sodium caproyl lactylate | 304,000 |
| Sodium lauroyl lactylate | 5,960 |

The data in Table 3 shows that foam stability and foam density is at an optimum for sodium caproyl lactylate. Tests on acyl lactylates have shown that foam structure changes from a stable spherical foam to an unstable hexagonal foam takes a longer time with increasing hydrocarbon chain length. For example, the foam viscosity, which is a measure of foam density and stability, increases substantially from a $C_6$ acyl lactylate to a $C_{10}$ acyl lactylate. For a $C_{10}$ acyl lactylate, a foam generated by stirring remains in the spherical form for more than 20 minutes.

It also was observed that the viscosity of a foam generated from sodium lauroyl lactylate increases over time, while the viscosity of a foam generated from the potassium salt of lauroyl lactylate decreases over time. Therefore, the potassium acyl lactylates are more suitable for the release of water and surfactants, and thus are preferred for use in shaving foams or soap bars. A comparison between sodium salts of different acyl lactylates further demonstrates the outstanding foam stability of the sodium caproyl lactylate.

The correlation between foam viscosity and foam structure is demonstrated in FIGS. 13–16, which illustrate the foam structure of aqueous solutions containing an acyl lactylate in combination with cocamidopropyl betaine in an 80/20 weight ratio of betaine to acyl lactylate. FIGS. 13–16 show that an optimum foam was generated from surfactant blends containing a combination of cocamidopropyl betaine and sodium caproyl lactylate. Visual examination of the foam structure using a microscope confirmed that good foam viscosity correlates to good foam structure.

Furthermore, incorporating a surfactant blend into an aqueous composition containing an anionic surfactant improves the foam properties of the resulting composition. In particular, the following compositions were prepared:

| | wt. %[4] |
|---|---|
| Sodium lauryl ether sulfate (5 moles of EO)[5] | 1.2 |
| Cocamidopropyl betaine | 5.2 |
| Acyl lactylate[6] | 1.6–0.5[7] |
| Deionized water | 81.0–82.1 |

[4]wt. % as active ingredients;
[5]EO is ethylene oxide;
[6]the acyl lactylates tested were sodium caproyl lactylate and MEA lauroyl lactylate; and
[7]the amount of acyl lactylate was varied over this range in different compositions.

Inspection of foams generated by these compositions showed that the best foam structure was obtained using 0.5 wt. % of MEA lauroyl lactylate. At this level, the MEA lauroyl lactylate modified the foam structure of cocamidopropyl betaine to essentially the identical foam structure exhibited in FIGS. 7 and 8, i.e., the foam structure of the standard SLS solution. In comparison, in the absence of an anionic surfactant, a 90/10 ratio of cocamidopropyl betaine and sodium caproyl lactylate provided the optimum foam structure. Accordingly, it is demonstrated that the identity and amount of acyl lactylate needed to generate an optimum foam varies with other ingredients present in the aqueous composition. However, determination of the identity and amount of acyl lactylate to incorporate into the present surfactant blend is easily determined by visual inspection of the foam.

Even more surprisingly, the foam structure of a composition containing 0.5 wt. % MEA lauroyl lactylate and 5.2 wt. % cocamidopropyl betaine even more closely matched the foam structure of the standard SLS solution after artificial sebum (0.10 wt. %) was added to the composition. This improvement in foam structure after the addition of sebum shows that the composition has an improved ability to remove a greasy soil from skin or hair.

It also was observed that incorporating a surfactant blend of the present invention into cleaning compositions improves the viscosity of the cleaning composition. In particular, a surfactant blend containing cocamidopropyl betaine and either sodium or MEA lauroyl lactylate was incorporated into an anionic surfactant-based composition as set out below:

| | Ex. 1 (wt. %[4]) | Ex. 2 (wt. %[4]) |
|---|---|---|
| Sodium lauryl ether sulfate (5 moles EO[5]) | 1.2 | 1.2 |
| Cocamidopropyl betaine | 5.2 | 5.2 |
| Sodium lauroyl lactylate | | 0.5, 1.0, 1.6 |
| MEA lauroyl lactylate | 0.5, 1.0, 1.6 | |
| Deionized water | 82.1, 81.6, 81.0 | 82.1, 81.6, 81.0 |

The viscosities of these solutions were measured and found to increase with increasing acyl lactylate concentration. This is an important effect because an increased solution viscosity provides a foam having an increased viscosity, which in turn correlates to a more stable foam structure.

With respect to the compositions of Ex. 2 containing sodium lauroyl lactylate, the following empirical formula correlates bulk viscosity of the composition to lactylate concentration:

$$\text{Bulk Viscosity} = (1.63)(e^{(503 \times LactyLate\ concentration)})$$

Figure 17:
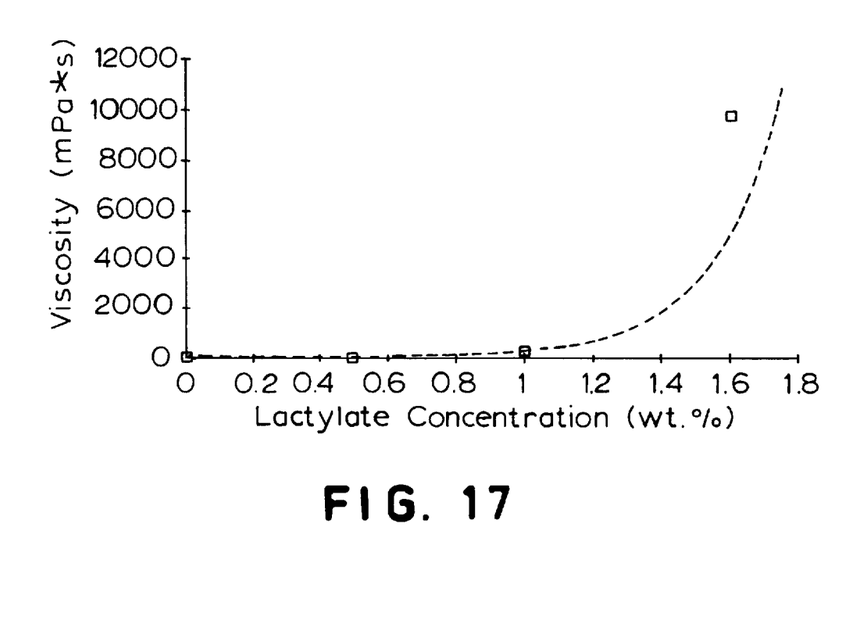
FIG. 17 is a plot of weight percent sodium lauroyl lactylate vs. viscosity, in mPa*s for compositions of Example 2.

The constants were determined for the formula of Ex. 2, and vary depending upon the particular formulation and acyl lactylate used in the formulation. Inparticular, the empirical formula was derived from the following data, which is presented in the plot of FIG. 17.

TABLE 4

| Sodium Lauroyl Lactylate Concentration in Formula of Ex. 2 | Viscosity of Bulk Composition (mPa*s) |
|---|---|
| 0 | 3 |
| 0.5 | 13 |
| 1.0 | 110 |
| 1.6 | 9,800 |

Figure 18:
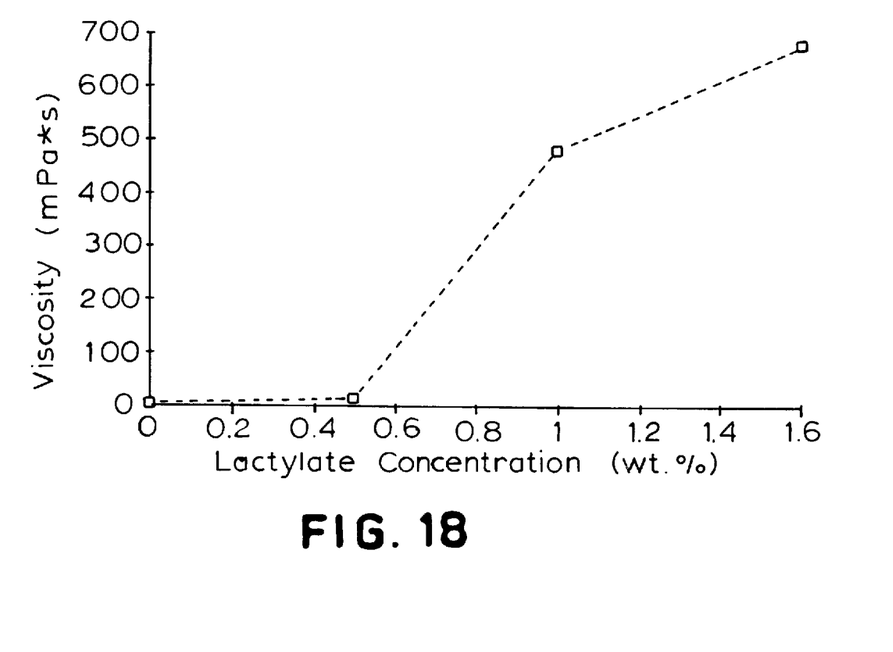
FIG. 18 is a plot of weight percent MEA lauroyl lactylate vs. viscosity, in mPa*s for compositions of Example 1.

Similarly, the compositions of Ex. 1 increase in viscosity with an increasing concentration of MEA lauroyl lactylate, but the effect of the acyl lactylate is less pronounced. The effects on viscosity by increasing the amount of MEA lauroyl lactylate in the composition of Ex. 1 are illustrated in Table 5 and FIG. 18.

TABLE 5

| MEA Lauroyl Lactylate Concentration in Formula of Ex. 1 | Viscosity of Bulk Composition (mPa*s) |
|---|---|
| 0 | 3 |
| 0.5 | 13 |
| 1.0 | 480 |
| 1.6 | 680 |

To illustrate the ability of acyl lactylates to improve the foam properties generated by a nonionic surfactant, and the usefulness of compositions having the ability to generate an improved foam, several different types of personal care compositions were prepared. In particular, surfactant blends of the present invention were incorporated into shaving foams, dentrifices, shampoos, shower gels, soaps, and hair care foams.

With respect to shaving foams, a surfactant blend containing sodium lauryl lactylate and an alkyl polyglycoside (i.e., GLUCOPON CS/UP, available from Henkel Corp., Hoboken, N.J.), can be used as a base for a shaving foam composition. The foam generated by the present surfactant blend is preferred over present-day commercial shaving foam compositions because it remains in the wet, spherical foam for a considerably longer time. A shaving foam incorporating a present surfactant blend therefore is able to deliver a better moisturizing effect, and to exhibit an efficacy similar to a shaving gel. In addition, the present surfactant blend had a foam viscosity of 85,000 mPa*s, whereas commercial foams have a viscosity of about 75,000 mPa*s. This is further evidence that a present surfactant blend provides a foam having an excellent density.

With respect to dentifrice compositions, such as toothpastes and gels, sodium lauryl sulfate generally is used as a foaming agent. However, SLS is known for its adverse affects on mucous membranes. The above-described surfactant blend, containing sodium lauroyl lactylate and an alkyl polyglucose, is a preferred foaming agent in dentifrice compositions because each ingredient is used in the food industry, and considered very safe. Furthermore, the present surfactant blends are clear, viscous liquids, which surprisingly maintain a high viscosity and clarity in polyols, like sorbitol, used in dentifrice compositions. In addition, glycerin does not adversely affect the clarity and viscosity of the surfactant blends. Finally, the present surfactant blends can be gelled with commonly used fumed silicas, and foam properties are not adversely affected.

With respect to shampoos and shower gels, it was found that acyl lactylates having a hydrocarbon chain length of $C_6$ to $C_{14}$, and especially $C_8$ to $C_{12}$, can be combined with amphoteric surfactants, like betaines, to produce excellent foam boosting and viscosity-increasing effects. In general, clear compositions which foam very well can be obtained. The preferred acyl lactylate was sodium caproyl lactylate. An aqueous blend containing sodium caproyl lactylate and an amphoteric surfactant provide an efficacious, yet gentle, shampoo that compares to commercial baby shampoos.

In addition, a surfactant blend containing an acyl lactylate and an alkyl polyglycoside provide an excellent shampoo or shower gel. The acyl lactylate provides a foam-boosting effect that makes such compositions consumer acceptable, even in the absence of high foaming anionic surfactant. As an additional benefit, although alkyl polyglycosides typically form opaque aqueous solutions, a present surfactant blend containing an alkyl polyglycoside forms aqueous solutions in the form of a clear, transparent gel. The gels have the ability to generate a copious, stable foam. Furthermore, although a surfactant blend containing an acyl lactylate and an alkyl polyglycoside generate an excellent foam in the absence of an anionic surfactant, such surfactant blends can be added to aqueous solutions containing an anionic surfactant to improve the foam properties and increase the viscosity of the solution.

As previously stated, the foaming properties of aqueous solutions of acyl lactylates having a hydrocarbon chain length of $C_8$ to $C_{12}$ are exceptional, with caproyl lactylate providing the best foam. Sodium caproyl lactylate and the other $C_8$ to $C_{12}$ acyl lactylates, therefore, are an excellent replacement for the sodium cocoyl isethionate commonly used in synthetic soap bars. The foam structure and foaming properties of the sodium cocoyl lactylate and sodium caproyl lactylate, in combination with a betaine, are denser than those of sodium lauryl sulfate. In addition, because the present surfactant blends are clear, and can be formed into essentially solid materials, the surfactant blends serve as an excellent base for clear, synthetic soap bars.

Many hair care compositions, like mousses and dyes, are formulated as foams. For the efficient delivery of actives such as conditioners, styling agents, or dyes to the hair, a spherical foam structure is needed. It was found that acyl lactylates in combination with a nonionic or amphoteric surfactant, like an alkyl polyglycoside or a betaine, produce spherical foams having sufficient stability for all hair care applications.

Overall, it has been shown that a surfactant blend of the present invention provides compositions having surprisingly high performance in applications where a copious, stable foam is required. The excellent foaming properties demonstrated by the surfactant blends were observed in viscosity measurements and by visual inspection of the foam under a microscope. It was found that acyl ($C_6$–$C_{14}$) lactylates, and especially acyl ($C_8$–$C_{12}$) lactylates, provide the improved foam properties. In particular, viscosity measurements show that acyl lactylates stabilize the foam density of amphoteric and nonionic surfactants, and that the foam becomes more stable and viscous (i.e., creamy) with increasing length of the hydrocarbon chain.

Acyl lactylates have shown an especially good ability to boost the foam generated by a betaine or by an alkyl polyglycoside. Sodium lauroyl lactylate and sodium caproyl lactylate have demonstrated an especially strong foam boosting effect on alkyl polycosides.

It should be understood that the foregoing detailed description is given merely by way of illustration. Obviously, many modifications and variations of the invention as hereinbefore set forth can be made without departing from the spirit and scope thereof, and, therefore, only such limitations should be imposed as are indicated by the appended claims.

What is claimed is:

1. A surfactant blend comprising:

(a) about 75% to about 99.9% by weight of a primary foaming agent selected from the group consisting of a nonionic surfactant, an amphoteric surfactant, and mixtures thereof; and (b) an acyl lactylate, wherein the acyl lactylate is present in a sufficient amount to provide a foam that remains in a spherical form for about two minutes to about 40 minutes, and wherein the surfactant blend is free of a sulfated anionic surfactant.

2. The surfactant blend of claim 1 comprising about 0.1% to about 25% by weight of the acyl lactylate.

3. The surfactant blend of claim 1 wherein the weight ratio of the primary foaming agent to the acyl lactylate is about 70:30 to about 90:10.

4. The surfactant blend of claim 1 wherein the nonionic surfactant has an HLB value of about 6 to about 25.

5. The surfactant blend of claim 1 wherein the nonionic surfactant is selected from the group consisting of an ether of a polyol and a sugar, a polyethylene glycol, a condensation product of ethylene oxide and a long chain ($C_8$–$C_{18}$) amide, a block copolymer of ethylene oxide and propylene oxide, an ethoxylated alcohol, an ethoxylated alkylphenol, an alkyl polyglycoside, and mixtures thereof.

6. The surfactant blend of claim 5 wherein the nonionic surfactant comprises an alkyl polyglycoside having a hydrophobic group containing 6 to 30 carbon atoms and a polysaccharide hydrophilic group containing about 1.5 to about 10 saccharide units.

7. The surfactant blend of claim 6 wherein the nonionic surfactant comprises an alkyl polyglycoside having the formula

$$RO\ (C_nH_{2n}O)_t(glycosyl)_x,$$

wherein R is selected from the group consisting of alkyl, alkylphenyl, hydroxyalkyl, hydroxyalkylphenyl, and mixtures thereof, wherein the alkyl group contains 10 to 18 carbon atoms; n is 2 or 3; t is a number from 0 to about 10; and x is a number from about 1.3 to about 10.

8. The surfactant blend of claim 1 wherein the amphoteric surfactant is selected from the group consisting of a betaine, an alkamidopropyl betaine, a sulfobetaine, an alkylamphocarboxylate, a phosphobetaine, a phosphitaine, an n-alkylamino propionate, an n-alkylamino dipropionate, and an imidazoline.

9. The surfactant blend of claim 1 wherein the primary foaming agent is selected from the group consisting of a betaine, an alkamidopropyl betaine, a sulfobetaine, an alkyl polyglycoside, an alkylamphocarboxylate, and mixtures thereof.

10. The surfactant blend of claim 1 wherein the acyl lactylate has a general structural formula:

wherein RCO is a $C_6$ to $C_{14}$ acyl radical; a is a number from 1 to 3; M is an alkali metal, an alkaline earth metal, ammonium, or a substituted ammonium group having one or more $C_1$ to $C_3$ alkyl or hydroxyalkyl groups.

11. The surfactant blend of claim 10 wherein RCO is a $C_8$ to $C_{12}$ acyl radical.

12. The surfactant blend of claim 1 wherein the acyl lactylate is selected from the group consisting of sodium lauroyl monolactylate, sodium myristoyl monolactylate, sodium decanoyl monolactylate, potassium dodecanoyl monolactylate, potassium dodecanoyl dilactylate, sodium myristoyl dilactylate, sodium lauroyl dilactylate, triethanolammonium, dodecanoyl monolactylate, ammonium decanoyl monolactylate, triethanolammonium decanoyl monolactylate, sodium caprooyl lactylate, sodium capryloyl lactylate, sodium caproyl lactylate, sodium cocoyl lactylate, sodium lauroyl lactylate, monoethanolammonium lauroyl lactylate, potassium lauroyl lactylate, and mixtures thereof.

13. An aqueous composition comprising the surfactant blend of claim 1.

14. The composition of claim 13 containing about 0.5% to about 15% by weight of the surfactant blend.

15. The aqueous composition of claim 13 selected from the group consisting of a shampoo, a shower gel, a hair conditioner, a mousse, a hair dye, a hair-styling aid, and a shaving cream.

16. A method of generating a stable, wet foam comprising:

(a) adding about 0.5% to about 15% by weight of a surfactant blend to an aqueous composition to provide an aqueous mixture, said surfactant blend comprising:
  (1) about 75% to about 99.9% by weight of a primary foaming agent selected from the group consisting of a nonionic surfactant, an amphoteric surfactant, and mixtures thereof, and
  (2) an acyl lactylate, wherein the acyl lactylate is present in a sufficient amount to provide a foam that remains in a spherical form for about two minutes to about 40 minutes, and wherein the surfactant blend is free of a sulfated anionic surfactant; and (b) forming bubbles from the aqueous mixture of step (a) to generate the stable foam.

* * * * *